United States Patent [19]

Broadwater et al.

[11] 4,331,154
[45] May 25, 1982

[54] BLOOD PRESSURE AND HEART RATE MEASURING WATCH

[75] Inventors: Ronald L. Broadwater, 2428 Eastridge Rd., Timonium, Md. 21903; Russell R. Haynes, Morgantown; Samah A. Mitry, Star City, both of W. Va.

[73] Assignees: Tech Engineering & Design, Morgantown, W. Va.; Ronald L. Broadwater, Sr., Timonium, Mo.

[21] Appl. No.: 84,961

[22] Filed: Oct. 15, 1979

[51] Int. Cl.³ .............................. A61B 5/02
[52] U.S. Cl. .................... 128/677; 128/690
[58] Field of Search .............. 128/677–683, 128/687–690

[56] References Cited

U.S. PATENT DOCUMENTS

| | | | |
|---|---|---|---|
| 3,717,140 | 2/1973 | Greenwood | 128/689 |
| 3,807,388 | 4/1974 | Orr et al. | 128/690 |
| 3,978,849 | 9/1976 | Gencen | 128/690 |
| 4,129,124 | 12/1978 | Thalmann | 128/690 |
| 4,190,886 | 2/1980 | Sherman | 128/681 |

OTHER PUBLICATIONS

"Silicon Transducer Strapped to Wrist Reads Blood Pressure", *Electronics* vol. 50, No. 9, Apr. 28, 1977, pp. 29-30.

Pratapa, Reddy, V.C.V., "All-Digital Instantaneous Heart Rate Meter", Med. & Biol. Engr. & Computing, vol. 15 1977, pp. 471-472.

*Primary Examiner*—Robert W. Michell
*Assistant Examiner*—Francis T. Jaworski
*Attorney, Agent, or Firm*—Pollock, Vande Sande & Priddy

[57] ABSTRACT

A digital watch is employed to measure systolic and diastolic blood pressure as well as heart rate. The band of the watch supports a piezoelectric transducer that is held in contact with the wrist adjacent to the radial artery when a switch on the band is activated. The watch contains electronic circuitry that derives a binary representation of the maximum or systolic pressure and the minimum or diastolic pressure that is generated at the artery by blood pressure pulses which can be displayed. Electronic circuitry is also provided to generate and address corresponding to the time interval T between successive measured heart beats. The address is used to access a memory device that contains a stored list of heart rates in cycles per minute. The contents of the memory at the address T corresponds to the reciprocal of T, in units of pulses per minute and a representation of the contents of the memory can be displayed.

16 Claims, 6 Drawing Figures

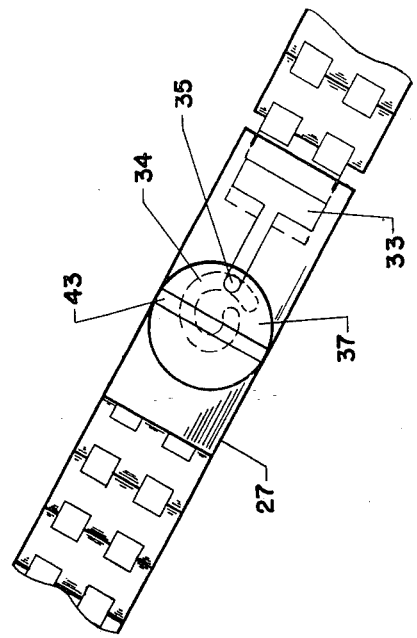
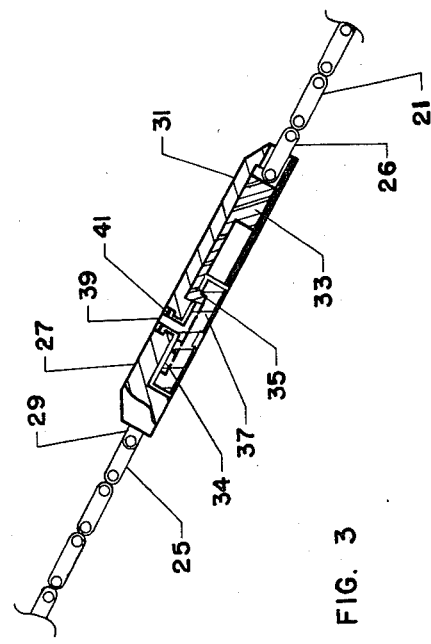

BLOOD PRESSURE AND HEART RATE MEASURING WATCH

DESCRIPTION

1. Technical Field

The invention relates to a wrist watch for measuring blood pressure and heart rate and, more particularly, to such a watch including relatively simple digital circuitry for measuring systolic and diastolic pressure and for measuring heart rate quickly and accurately.

2. Background Art

Heart rate and blood pressure are important factors in determining the state of a person's health and the physical condition of a person's body in response to physical or emotional stress. A periodic monitoring of these physical parameters is particularly important for individuals having cardiac afflictions or high blood pressure. However, physically healthy individuals may also desire to periodically monitor their heart rate and blood pressure in stress situations, for example when engaging in strenuous exercise.

Thus, there is a need for an apparatus that will conveniently and quickly measure the heart rate and blood pressure of an individual and that will not require an undue amount of training to operate. Also, it is important that such an apparatus be compact and unobtrusive in use so that it may be easily used in a variety of circumstances.

Accordingly, heart rate and blood pressure measuring apparatus, in accordance with the invention, is mounted in a wrist unit that is also used to tell time. Electronic circuitry in the unit is employed to measure the rate and force of blood pressure pulses that pass through the radial artery of the wrist. The unit then provides a digital display of the heart rate in pulses per minute and the systolic and diastolic blood pressure in millimeters of mercury.

Wrist-mounted heart rate monitors are known to the art and have been disclosed, for example, in the U.S. patent to Orr et al, U.S. Pat. No. 3,807,388, wherein the duration of a heart beat is measured by counting electrical pulses recurring at a known frequency. The duration of the heart beat is then related to a particular average heart beat rate. However, the measurement system of Orr et al does not directly measure the heart rate and, therefore, is subject to inaccuracies of measurement due to the instability of heart beat duration over brief intervals of time.

There is also disclosed in the patent to Prinz, U.S. Pat. No. 4,120,296 a heart rate measuring wrist watch wherein electrical pulses having a particular frequency are generated over the intervals between heart pulses and are applied to a counter, the contents of the counter being stored for display and the counter being cleared every 15 seconds to provide new heart rate data. However, the apparatus of Prinz is fairly complicated and is also subject to errors resulting from the operational drift of an integrator and associated voltage sensitive oscillator that are employed to generate the electrical timing pulses that are counted between the heart rate pulses.

Accordingly, it is an object of the invention to provide a relatively simple and accurate apparatus for noninvasively measuring the heart rate of an individual.

Another object of the invention is to provide such a heart rate measuring apparatus that may be mounted in a wrist watch and employed to provide a digital display of heart rate in pulses per minute.

It has been suggested in the patent to M. J. Campanella, U.S. Pat. No. 2,756,741, that an indication of systolic blood pressure may be obtained by employing a wrist-mounted apparatus to analyze the intensity of the blood pressure pulses that pass through the radial artery of a wrist. A piezoelectric transducer is applied adjacent to the radial artery of the wrist to generate electrical signals corresponding to the blood pressure pulses that pass through the artery. The electrical signals from the transducer are applied to a vacuum tube circuit that includes a peak detector that generates a voltage corresponding to the systolic pressure occurring at the peak of each blood pressure pulse. The peak detected signal is applied to a difference amplifier and an associated meter that indicates the change of the detected systolic pressure with respect to a normal, calibrated blood pressure.

The blood pressure measuring apparatus of Campanella is not employed to measure diastolic blood pressure and, also, the vacuum tube signal analyzing circuitry of Campanella is bulky and requires substantial power to operate.

A blood pressure measuring apparatus is disclosed in the patent to Petzke et al, U.S. Pat. No. 3,926,179, wherein a probe is applied adjacent the radial artery of a wrist. A pressure-sensitive transducer on the probe generates electrical signals corresponding to the blood pressure pulses of the radial artery. The electrical pulses are applied to analog circuitry that generates a systolic signal corresponding to the integrated voltage at the peak of the electrical pulse signal and a diastolic signal corresponding to the voltage at the low point of the pulse signal. The analog apparatus of Petzke et al requires a substantial amount of power to operate and, therefore, is not suitable for use in a watch that may be worn on the wrist.

Accordingly, it is an object of the invention to provide a relatively simple and low power electronic apparatus that may be mounted in a watch to analyze measure blood pressure pulses at the radial artery of the wrist and to thereby derive values for systolic and diastolic blood pressure.

These and other objects of this invention will become apparent from a review of the detailed specification which follows and a consideration of the accompanying drawings.

DISCLOSURE OF THE INVENTION

In order to achieve the objects of the invention and to overcome the problems of the prior art, the blood pressure and heart rate measuring watch, in accordance with the invention, includes a piezoelectric transducer that is supported on a wrist band adjacent to the radial artery of the wrist. The transducer generates electrical pressure pulses with amplitudes that correspond to the magnitude of the blood pressure pulses of the radial artery. The maximum voltage of the electrical pulses corresponds to the systolic pressure within the artery and the minimum voltage corresponds to the diastolic pressure.

An analog to digital convertor samples the voltage amplitude at a plurality of points on each of the electrical pulses and generates corresponding coded data words. A comparator means compares the coded data words and stores the data word having the highest value and the data word having the lowest value. The minimum and maximum data words are displayed to indicate the diastolic and systolic pressure.

A counter is employed to register the time interval between successive electrical pressure pulses as a count state that corresponds to the number of clock pulses of a particular frequency that are generated over the interval between the pressure pulses. The count state of the counter is applied as an address to access a heart rate data word in a ROM memory. The accessed data word defines a heart rate that will produce blood pressure pulses having the time interval defined by the accessing count state. The accessed heart rate data word of the ROM memory is then displayed.

BRIEF DESCRIPTION OF THE DRAWINGS

FIG. 1b illustrates the face of the watch of FIG. 1a.

FIG. 2 illustrates a side elevation view of the transducer support and control switch for the watch of FIG. 1a.

FIG. 3 illustrates a side elevation view of a tension adjustment apparatus for the band of the watch of FIG. 1a.

FIG. 4 illustrates a bottom elevation view of the tension adjustment apparatus of FIG. 3.

FIG. 5 illustrates a block diagram of a circuit for operating the watch of FIG. 1a.

BEST MODE FOR CARRYING OUT THE INVENTION

Figure 1A:
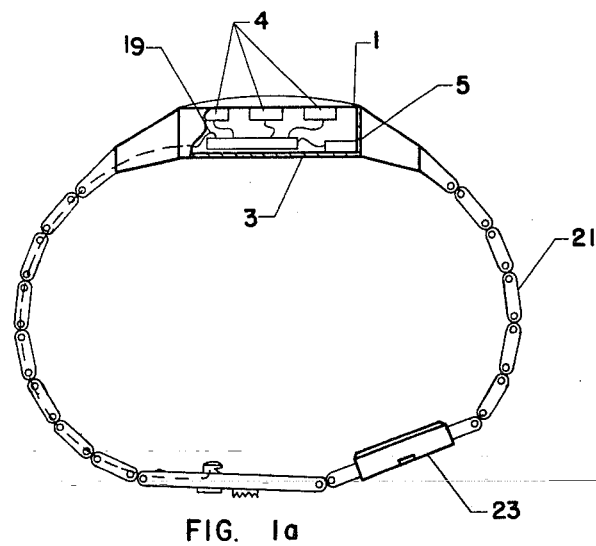
FIG. 1a illustrates a side elevation view in partial section of the heart rate and blood pressure measuring watch in accordance with the invention.

The remaining portion of this specification will describe preferred embodiments of the invention when read in conjunction with the attached drawings, in which like reference characters identify identical apparatus.

FIG. 1a illustrates a side elevation view in partial section of a blood pressure and heart rate measuring watch, in accordance with the invention. A watch case 1 contains electronic circuitry 3 that is employed to register the time and also to generate electrical signals corresponding to the blood pressure and heart rate of the wearer. The watch case 1 also contains a power source, for example a battery 5, that powers the electronic circuitry 3 and associated 7-segment type digital displays 4.

Figure 1B:

FIG. 1b illustrates the face of the digital display of the watch in accordance with a preferred embodiment of the invention. The topmost portion of the display shows the time in hours and minutes, a middle portion shows the systolic and diastolic pressure separated by a slash mark and the bottom portion of the display shows the heart rate in pulses per minute. It should be appreciated that the display of FIG. 1b may be comprised of either conventional 7-segment light emitting diode elements or liquid crystal display elements. As shown in FIG. 1a, the digital display and associated electronic circuitry and battery are enclosed by a transparent crystal of a known type.

In normal operation, the time measuring circuitry of the watch of FIG. 1a operates in a conventional manner to provide electrical signals corresponding to the time. The watch casing 1 may include a button for selectively activating the time display for a particular period of time, in order to conserve the power of the battery 5. Of course, if the display is a liquid crystal display, the time indication may be continuously shown since very little power is required to operate the display.

Figure 2:
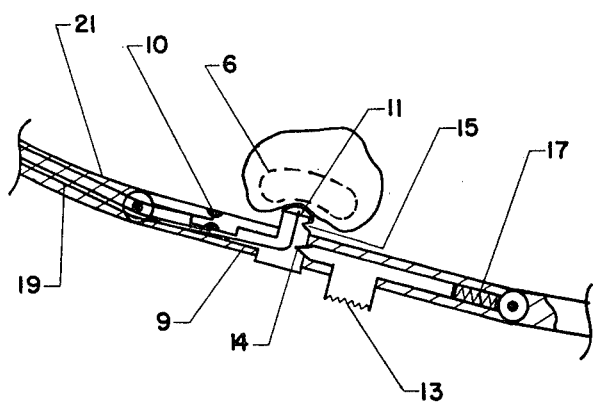

As shown in FIG. 2, the blood pressure and pulse rate circuitry and associated display elements of the watch are activated by pressing inwardly on a hinged transducer support arm 9 having a pressure transducer 11 mounted on an inwardly extending portion of the arm. As the transducer support arm 9 is pressed inwardly, the pressure transducer 11 is forced into contact with the skin of the wrist adjacent to the radial artery 6 of the wrist. The inward movement of the support arm activates a micro switch 10 that applies power to the blood pressure and pulse rate circuitry and associated displays over power leads 19 that may be embedded or woven in the material of a watch band 21. A sliding switch 13 is then engaged with an outer notch 14 of the arm 9 so that the transducer 11 is held adjacent to the radial artery. The sliding switch 13 is biased by a spring 17 so that the switch will remain in engagement with the outer notch 14 and will thereby maintain the support arm and transducer in an engaged, pressing relation with the radial artery.

As shown in FIG. 1a, the micro switch 10 is deactivated and the blood pressure and pulse rate measuring circuitry and associated displays are thereby de-energized when the transducer 11 is disengaged from the radial artery by moving the support arm 9 outwardly from the wrist and engaging the switch 13 with an inner notch 15. It should be understood that although the watch band 21 of FIG. 1a is shown as a chain-link band, other types of bands may be employed without departing from the spirit of the invention.

The pressure transducer 11 may suitably be comprised of a piezoelectric crystal that generates an electrical signal having a voltage amplitude that corresponds to the magnitude of applied pressure. Thus, when the heart of the wearer of the watch contracts, a strong pulse of blood is passed through the radial artery, thereby causing the artery to expand and exert a pressure on the piezoelectric pressure transducer 11. The pressure on the piezoelectric transducer will increase to a maximum point, corresponding to the maximum contraction of the heart and, thereafter, the pressure will decrease as the heart expands and the walls of the radial artery contract.

It should be understood that the high internal pressure of the artery at the point of maximum contraction of the heart is the systolic pressure and the lower pressure within the artery at the point of maximum expansion of the heart is the diastolic pressure. Accordingly, the piezoelectric transducer 11 will register an electrical pulse corresponding to each contraction and subsequent expansion of the heart and the voltage at the peak of the electrical pulse will correspond to the systolic pressure, while the low point of the pulse will correspond to the diastolic pressure.

Although a piezoelectric crystal has been utilized as a pressure transducer in a preferred embodiment of the invention, it should be appreciated that other transducers known to the art may be employed without departing from the spirit of the invention. However, the piezoelectric transducer is desirable for this application since the transducer measures the direct effect of the pressure exerted within the radial artery, while other transducers, for example resistive strain gauges, measure secondary effects such as the strain forces that are applied at the surface of the skin due to the expansion of the radial artery.

Although there is only a fairly thin layer of tissue covering the radial artery of the average wrist, the force exerted by the radial artery in response to blood pressure pulses is sufficiently small to require that the piezoelectric transducer 11 be held in contact with the wrist at a fairly precise pressure so that the blood pressure pulse is properly registered. In the U.S. patent to Petzke et al, U.S. Pat. No. 3,926,179, it is indicated that blood pressure pulse signals may be maximized by providing a pressure on the radial artery that is sufficient to flatten the artery approximately half-way. In addition to maximizing the blood pressure signals from the artery, the partial flattening of the artery also causes the circumferential tension in the elastic wall of the artery to act in a direction that is perpendicular to the radial pulses of the blood pressure, so that the circumferential tension does not cause inaccuracies in the magnitude of the pulse pressure.

Since individual wrists vary in size and since the skin thickness of wrists also varies, it is necessary to provide a means for adjusting the critical pressure of engagement of the piezoelectric transducer 11 and the radial artery in accordance with the physical characteristics of the wrist of the wearer of the watch. Thus, as shown in FIG. 1a, a tension adjustment apparatus 23 is provided for the wrist band 21 of the watch in order to adjust the size of the band and to thereby adjust the pressure at which the transducer 11 is applied to the radial artery when the sliding switch 13 is engaged with the outer notch 14 of the support arm 9.

FIGS. 3 and 4 illustrate a tension adjustment apparatus that may be used to adjust the size of the wrist band 21 in a preferred embodiment of the invention. As shown in FIG. 3, the wrist band 21 may be comprised of links and a connected adjustment housing 27. One end 29 of the adjustment housing 27 is affixed to an end of a link 25 and the opposite end 31 of the adjustment housing 27 is open to admit an associated end link 26 that is affixed to a cam follower 33 that is slidably supported within the adjustment housing. A tab end 35 of the cam follower 33 is engaged with a spiral groove 34 formed in a cam 37 that is mounted for rotation about a shaft 39 within the housing 27. A retainer clip 41 may be affixed at the end of the shaft 39 to hold the cam 37 in a rotatably supported position within the adjustment housing 27.

As shown in FIG. 4, the outward face of the cam 37 has a slot 43 that may be engaged by a screwdriver, coin, or other thin object to rotate the cam 37. It should be understood that as the cam 37 rotates, the tab end 35 of the cam follower 33 will follow the groove 38 in the cam 37 and will thereby cause the cam follower 33 to be slidably moved either inwardly or outwardly with respect to the adjustment housing 27, in accordance with the direction of rotation of the cam 37. Thus, the pressure of engagement of the piezoelectric transducer 11 and the radial artery of the wrist is set by adjusting the tension of the wrist band 21.

It should be appreciated that the tension of the wrist band 21 must be initially adjusted to correspond to the size of a particular person's wrist and the circuitry of the invention must then be calibrated to display proper pressure readings. Of course, a subsequent adjustment must be made if the size of an individual's wrist changes, for example if the individual loses or gains a substantial amount of weight.

Figure 5:
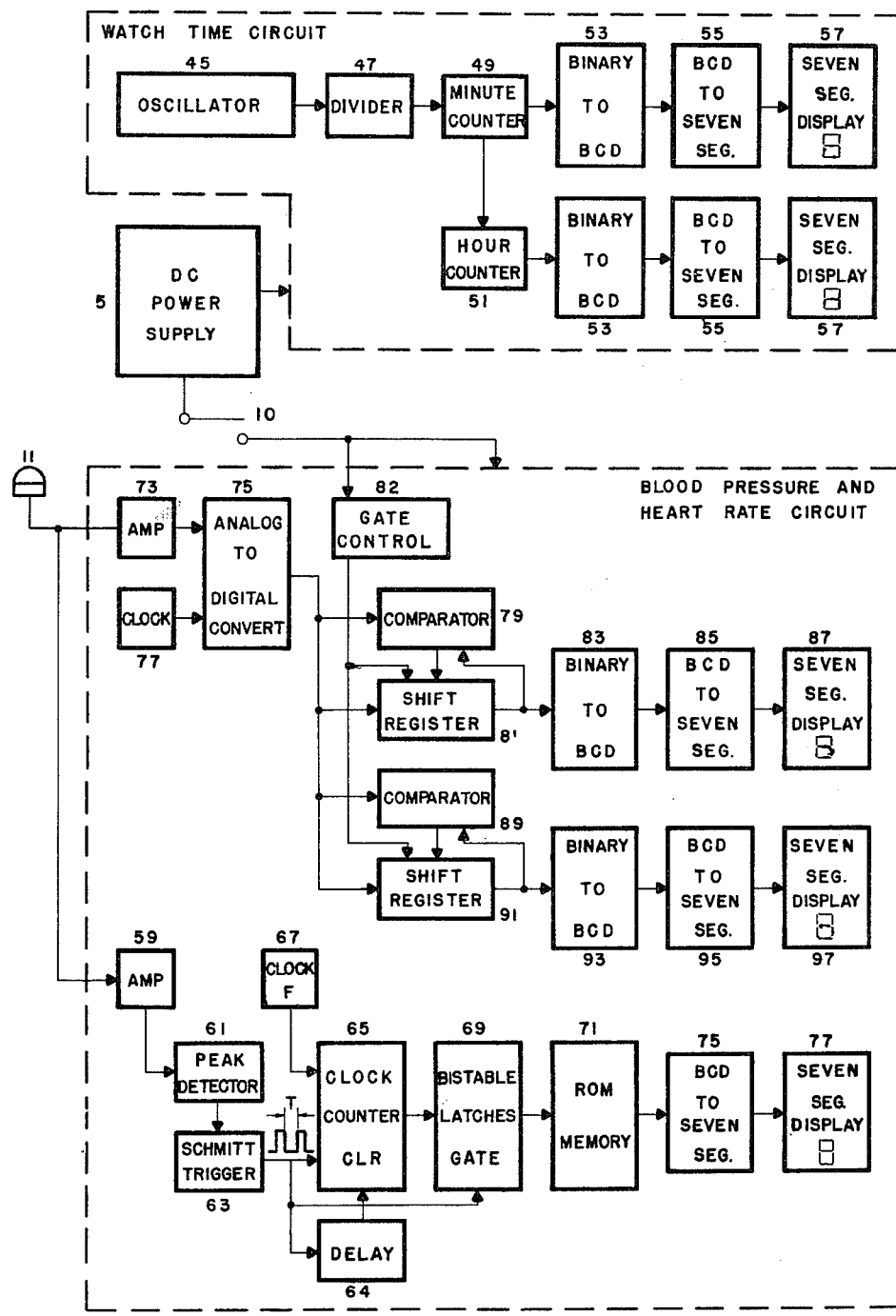

FIG. 5 illustrates a block diagram of an electronic circuit that may be employed to provide the time registration function and blood pressure and heart rate measurement function in accordance with the invention. The time registration circuitry corresponds to circuitry typically available in commercial digital wrist watches. The time circuit includes a crystal controlled oscillator 45 that generates, for example, a 16 KHz signal that is applied to a corresponding divider 47 having a tap-off point at which a pulse is generated each minute. The minute pulses are applied to a minute counter 49 that defines a 59 count cycle and the overflow bit of the minute counter is applied to an hour counter 51 that defines a 12 count cycle. The binary outputs of the minute counter 49 and hour counter 51 are applied to corresponding binary to BCD decoders 53 that connect with BCD to seven-segment decoders 55 and seven-segment displays 57. It should be appreciated that although particular circuit components have been described with respect to the clock circuit of the invention, other known components or circuits may be employed without departing from the spirit of the invention.

In accordance with the invention, the heart rate of the wearer is measured by applying the electrical input signal from the piezoelectric pressure transducer 11 to an amplifier 59 having an adjustable gain. The gain of the amplifier 59 is adjusted to generate a signal having a voltage swing that is within the detection range of a corresponding peak detector circuit 61.

The peak detector circuit 61 may operate in accordance with the description provided in "Linear Integrated Circuits National", pgs. 3-20 (February, 1975). The peak detector circuit 61 generates a signal in response to a particular value of input voltage. Thus, the peak detector circuit 61 will generate a signal when the voltage at the output of the amplifier 59 reaches a particular predetermined level. The signal at the output of the peak detector circuit 61 is applied to a schmitt trigger 63 that generates a corresponding electrical counting pulse. Thus, it should be understood that the schmitt trigger 63 generates an electrical counting pulse for each blood pressure pulse that is registered by the transducer 11. The peak detector circuit 61 ensures that the schmitt trigger 63 will not be triggered by brief noise pulses that momentarily rise to a triggering voltage level.

The triggering pulse of the schmitt trigger 63 is applied through a delay 64 to the clear input of a counter 65 and to the gate inputs of associated bistable latches 69. The clock input of the counter 65 is connected to the output of a counter clock 67 that may be derived from the divider 47 or that may be generated by a separate adjustable oscillator.

When the piezoelectric transducer 11 is initially moved into contact with the radial artery of a wrist, the micro switch 10 closes to apply power to the blood pressure and heart rate circuit and the first heart pulse causes the schmitt trigger to generate a trigger pulse that gates the contents of the counter 65 into the bistable latches 69 and, thereafter, clears the counter. The cleared counter then begins counting the pulses that are generated by the counter clock 67 at a particular count frequency F. When the second heart pulse causes a second trigger pulse to be generated by the schmitt trigger 63, the number of pulses that were counted between the first heart pulse and the second heart pulse are stored in the bistable latches 69 and the counter is again cleared to begin counting pulses from the clock 67. Thus, after each trigger pulse, the bistable latches have stored the number of clock pulses that were counted between the current and previous trigger pulse.

The count data stored in the bistable latches 69 is applied to the address input of a programmed read only memory (ROM) 71. Thus, the memory is accessed at an address location that corresponds to the time interval or period T between successive heart pulses. Thus, for the time T in seconds and, given a frequency F of the counter clock 67 in pulses per second, the accessed address in the memory 71 is F·T.

The contents of the memory location F·T should correspond to a heart rate, in pulses per minute that will produce heart pulses having a period T. Therefore, the contents of the memory at the indicated address should correspond to 60/T. It should be understood that the accuracy of the heart rate measurement is dependent, in part, upon the available storage capacity of the memory 71 and the associated frequency of the counter clock 67.

As an example, if the possible range of heart rates is from 30 pulses per minute to 120 pulses per minute, the corresponding measured period T between heart beats ranges from 2 seconds to 0.5 seconds. If the desired accuracy of time measurement is 0.01 seconds, the frequency of the counter clock 67 should be adjusted to 100 pulses per second. Thus, for a heart rate of 30 beats per minute, 200 pulses are counted in the counter 65 between heart beats and for a heart rate of 120 beats per minute, 50 counts are registered in the counter 65 between successive heart beats. Accordingly, the expected range of pulse states of the counter 65 is from 50 to 200.

A coded representation corresponding to the heart rate of 30 beats per minute is stored at the address 200 and a coded representation of a heart rate of 6000/199 is stored at the next address 199. In general, at each address x of the memory 71, a coded representation of a heart rate of 6000/x is stored. For a system having the count frequency F, a count state x of the counter 65 will access a stored coded representation in the memory 71 corresponding to a heart rate of (F/x)·(60).

It should be understood that the heart rate circuit of FIG. 5 may be easily modified to allow the counter 65 to accumulate a count for a plurality of heart beat intervals. For example, an auxiliary counter may be employed to operate the counter 65 so that count pulses from the clock 67 are accumulated over a particular number of heart beats. Of course, the data in the memory 71 must then be adjusted to take into account the increased number of heart beats over which an accumulated count is taken.

If the data in the momory 71 is comprised of binary representations of the indicated range of heart beat values, a binary to BCD decoder and BCD to seven-segment decoder will be required to display the accessed heart rate values on the seven-segment displays 77. The conversion steps may be avoided if seven-segment representations of heart beat values are stored in the momory 71. Thus, if seven-segment coding is utilized for the heart beat values stored in the memory, the output of the memory may be applied to the seven-segment displays through appropriate drivers. Alternatively, the heart beat values may be programmed into the store as BCD values, thereby avoiding the BCD decoding step and requiring only a BCD to seven-segment decoder 75 to apply the heart rate data to the seven-segment displays 77.

It should be appreciated that the programmed read only memory in the heart rate computation circuit of FIG. 5 is employed to ensure that heart rate amounts are generated quickly and accurately. Also, the memory is not subject to errors caused by the expected operational drift of electronic components over time.

It should be understood that the above-described circuit elements of the heart rate measuring circuit of FIG. 5 are intended to be included as functional components of an integrated circuit chip. Thus, the physical size of the circuit elements of FIG. 5 may be reduced in a manner known to the art to fit within the relatively small area contemplated for use in the watch casing of FIG. 1a.

A portion of the circuit of FIG. 5 is directed to deriving a measurement of the systolic and diastolic blood pressure from the electrical pulse signal that is generated by the piezoelectric transducer 11. In operation, the transducer 11 is pressed into contact with the radial artery, the sliding switch 13 is engaged with the outer notch 14 and the micro switch 10 is closed to energize the blood pressure and heart rate circuit.

The voltage pulses from the transducer 11 are then applied to an amplifier 73 having an adjustable gain and the amplifier passes amplified pulses to an analog to digital converter 75. The voltage gain of the amplifier 73 is adjusted to provide pulses with a voltage swing within the operational range of the analog to digital converter 75. The converter 75 receives the analog voltage pulse of the amplifier and a gating signal from a millisecond clock 77 that may be taken from the divider 47 or generated by an independent oscillator.

The gating clock 77 is adjusted to generate several thousand pulses per second, and the pulses are applied by the converter to sample the voltage at many points on each output pulse of the amplifier 73. Each of the sampled voltages is then converted to a binary code that corresponds to the pressure in millimeters of mercury that was applied to the transducer 11 to produce the sampled voltage at the output of the amplifier 73.

The binary code for the initial voltage sample of a pulse from the amplifier 73 is applied to a first input of a comparator 79 and is stored in a shift register 81 in response to a pulse from a gate control citrcuit 82 that is activated by the miro switch 10. The output of the shift register 81 is applied to a second input of the comparator 79 and to binary to BCD decoders 83. The outputs of the decoders 83 are applied to corresponding BCD to seven-segment decoders 85 and the outputs of the decoders 85 are then applied to corresponding seven-segment displays 87.

After the first sample from the converter 75 is applied to the comparator 79 and gated into the shift register 81, the binary code of the second sample is applied to the input of the comparator 79 and, if the magnitude of the binary code of the second sample is greater than the magnitude of the binary code of the first sample, the comparator 79 operates to store the larger binary code of the second sample in the shift register 81 by overwriting the previously stored code.

Successive binary codes are applied to the comparator 79 and are compared with the code stored in the shift register 81, and, if the code in the shift register is smaller, the larger code is stored in the shift register by overwriting the smaller stored code. Thus, the shift register 81 is operated to store a maximum binary code that corresponds to the maximum blood pressure that is measured by the transducer 11 and the maximum code is displayed on the seven-segment display 87. It should be understood that the maximum code stored in the shift register 81 corresponds to the pressure in millimeters of mercury that is measured by the piezoelectric transducer 11 at the peak or systolic point of the blood pressure pulses. Thus, the seven-segment displays 87 show the measured systolic blood pressure.

The diastolic blood pressure is measured in a fashion that is similar to the measurement of the systolic blood pressure. In operation, the binary coded signal for the initial sample is stored in a shift register 91 and is applied to a comparator 89. Successive samples are applied to the comparator 89 and are compared with the contents of the shift register 91. When the contents of the shift register 91 and a binary code applied at the comparator 89 are compared, the comparator 89 operates to store the smaller compared code in the shift register 91, by overwriting any previously stored code. Therefore, over a period of time, the shift register 91 accumulates the smallest binary code, corresponding to the pressure in millimeters of mercury of the low or diastolic point of the blood pressure pulses measured by the transducer 11. The output of the shift register 91 is applied to binary to BCD decoders 93 and the outputs of the decoders 93 are applied to corresponding BCD to seven-segment decoders 95 that apply their corresponding outputs to associated seven-segment displays 97. Thus, the seven-segment displays 97 are operated to display the measured diastolic blood pressure.

It should be understood that the elements of the blood pressure measuring circuit of FIG. 5 are intended to be included as components of a chip having dimensions sufficiently small to fit within the watch casing 1. Also, it should be understood that the blood pressure measuring circuit of FIG. 5 must be calibrated to a particular individual in order to provide an accurate read-out of blood pressure. Accordingly, the watch of FIG. 1a must be placed on the intended user's wrist and the tension of the watch band must then be adjusted to provide an optimum contact pressure between the transducer 11 and the radial artery. Thereafter, the individual's blood pressure must be taken by any accurate means known to the art and the amplifier 73 must then be adjusted to provide a matching blood pressure read-out on the displays 87 and 97. Subsequent re-calibration may be occasionally required to compensate for unavoidable changes in the tension of the watch band over time or in the physical condition of the user's wrist.

The invention may be embodied in other specific forms without departing from its spirit or essential characteristics. The present embodiments are, therefore, to be considered in all respects as illustrative and not restrictive, the scope of the invention being indicated by the claims rather than by the foregoing description and all changes which come within the meaning and range of the equivalents of the claims are therefore intended to be embraced therein.

We claim:

1. Apparatus for measuring blood pressure, comprising:
    transducer means for generating an electrical signal having an amplitude corresponding to the magnitude of applied pressure;
    means for pressing at least a portion of said transducer means adjacent an area of a body where blood pressure pulses may be detected, the transducer means generating electrical pressure pulses corresponding to the detected blood pressure pulses, each of the electrical pressure pulses defining a maximum voltage over a systolic interval and a minimum voltage over a diastolic interval;
    analog to digital converter means for sampling the voltage amplitude at a plurality of points on each electrical pressure pulse and for generating a coded data word for each sampled voltage, the data word defining the pressure corresponding to the sampled voltage amplitude;
    systolic comparator means for comparing said coded data words and storing the data word defining the highest pressure;
    diastolic comparator means for comparing said coded data words and storing the data word defining the lowest pressure; and
    pressure display means for displaying a representation of the stored data word of the systolic comparator and of the diastolic comparator.

2. The apparatus of claim 1 wherein said transducer means includes a piezoelectric crystal.

3. The apparatus of claim 1 wherein said systolic comparator means includes:
    shift register means for storing only one coded data word of said analog to digital converter means at a particular instant of time;
    means for storing in said shift register means the first coded data word generated by said analog to digital converter means, and
    means for comparing the coded data word stored in said shift register means with a coded data word generated by said analog to digital converter means and for storing the coded data word of said analog to digital converter means in said shift register means if the coded word in said shift register means is less than the coded data word of said analog to digital converter means.

4. The apparatus of claim 1 wherein said diastolic comparator means includes:
    shift register means for storing only one coded data word of said analog to digital converter means at a particular instant of time,
    means for storing in said shift register means the first coded data word generated by said analog to digital converter means, and
    means for comparing the coded data word stored in said shift register means with a coded data word generated by said analog to digital converter means and for storing the coded data word of said analog to digital converter means in said shift register means if the coded data word in said shift register means is greater than the coded data word of said analog to digital converter means.

5. The apparatus of claim 1 which is adapted for measuring heart rate, in addition to blood pressure and comprising:
    counter means for measuring the time interval between successive electrical pressure pulses for generating coded addresses, each address representative of the total magnitude of a fixed number of associated measured time intervals, the fixed number being at least one;
    memory means having a stored data table of heart rate codes, each heart rate code being stored for access by an associated one of said coded addresses and each heart rate code defining a value of heart rate that will produce blood pressure pulses having the time interval represented by the associated one of the coded addresses;

means for applying each coded address to access said memory means for at least a time prior to the generation of a next successive coded address by said counter means; and heart rate display means for displaying a heart rate representation of the accessed heart rate code in said memory means.

6. The apparatus of claim 5 wherein said counter means includes:

trigger means for generating an electrical trigger pulse in response to a particular voltage level of each electrical pressure pulse, timing means for registering a count state defining the time interval between trigger pulses, the timing means responsive to a trigger pulse to clear and begin counting at a particular frequency, and bistable latch means responsive to a trigger pulse for storing the count state of said timing means before the timing means is cleared, the stored count state in the bistable latch means being applied as a coded address to access said memory means.

7. The apparatus of claim 6 wherein said trigger means includes a peak detector and a schmitt trigger.

8. The apparatus of claim 5 wherein said memory means is a read only memory.

9. The apparatus of claim 5 wherein said means for pressing includes means for pressing a pressure sensitive portion of said transducer means adjacent the radial artery of a wrist.

10. The apparatus of claim 5 including means for registering the passage of time and for displaying the time.

11. Apparatus for measuring heart rate and blood pressure, comprising:

transducer means for generating an electrical signal having an amplitude corresponding to the magnitude of applied pressure;

means for pressing at least a portion of said transducer means adjacent an area of a body where blood pressure pulses may be detected, the transducer means generating electrical pressure pulses corresponding to the detected blood pressure pulses, each of the electrical pressure pulses defining a maximum voltage over a systolic interval and a minimum voltage over a diastolic interval;

means for generating a coded representation of the pressure corresponding to the maximum voltage generated by said transducer means in response to said blood pressure pulses and for displaying the coded representation as the systolic pressure;

means for generating a coded representation of the pressure corresponding to the minimum voltage generated by said transducer means in response to said blood pressure pulses and for displaying the coded representation as the diastolic pressure;

counter means for measuring the time interval between successive electrical pressure pulses and for generating coded addresses, each address representative of the total magnitude of a fixed number of associated measured time intervals, the fixed number being at least one;

memory means having a stored data table of heart rate codes, each heart rate code being stored for access by an associated one of said coded addresses and each heart rate code defining a value of heart rate that will produce blood pressure pulses having the time interval represented by the associated one of the coded addresses;

means for applying each coded address to access said memory means for at least a time prior to the generation of a next successive coded address by said counter means; and rate display means for displaying a heart rate representation of the accessed heart rate code in said memory means.

12. A wrist watch for registering the time and for measuring heart rate and blood pressure from the blood pressure pulses of the radial artery of the wrist, comprising:

transducer means for generating an electrical signal having an amplitude corresponding to the magnitude of applied pressure;

means for pressing at least a portion of said transducer means adjacent to the radial artery, the transducer means generating electrical pressure pulses corresponding to the detected blood pressure pulses, each of the electrical pressure pulses defining a maximum voltage over a systolic interval and a minimum voltage over a diastolic interval;

analog to digital converter means for sampling the voltage amplitude at a plurality of points on each electrical pressure pulse, and for generating a coded data word for each sampled voltage, the data word defining the pressure corresponding to the sampled voltage amplitude;

systolic comparator means for comparing said coded data words and storing the data word defining the highest pressure;

diastolic comparator means for comparing said coded data words and storing the data word defining the lowest pressure;

pressure display means for displaying a representation of the stored data word of the systolic comparator and of the diastolic comparator;

counter means for measuring the time interval between successive electrical pressure pulses and for generating coded addresses, each address representative of the total magnitude of a fixed number of associated measured time intervals, the fixed number being at least one;

memory means having a stored data table of heart rate codes, each heart rate code being stored for access by an associated one of said coded addresses and each heart rate code defining a value of heart rate that will produce blood pressure pulses having the time interval represented by the associated one of the coded addresses;

means for applying each coded address to access said memory means for at least a time prior to the generation of a next successive coded address by said counter means; and rate display means for displaying a heart rate representation of the accessed heart rate code in said memory means.

13. The wrist watch of claim 12 wherein said means for pressing includes an adjustable wrist band.

14. The wrist watch of claim 12 wherein said means for pressing includes switch means for applying power to the analog to digital converter means, systolic and diastolic comparator means, pressure display means, counter means, memory means, means for applying and rate display means when said transducer is engaged adjacent the radial artery.

15. The apparatus of claim 12 wherein said systolic comparator means includes:

shift register means for storing only one coded data word of said analog to digital converter means at a particular instant of time;

means for storing in said shift register means a first coded data word generated by said analog to digital converter means, and means for comparing the coded data word stored in said shift register means with a coded data word generated by said analog to digital converter means and for storing the coded data word of said analog to digital converter means in said shift register means if the coded word in said shift register means is less than a coded data word of said analog to digital converter means.

16. The apparatus of claim 12 wherein said diastolic comparator means includes:

shift register means for storing only one coded data word of said analog to digital converter means at a particular instant of time, means for storing in said shift register means the first coded data word generated by said analog to digital converter means, and means for comparing the coded data word stored in said shift register means with a coded data word generated by said analog to digital converter means and for storing the coded data word of said analog to digital converter means in said shift register means if the coded word in said shift register means is greater than the coded data word of said analog to digital converter means.

* * * * *